(12) United States Patent
Tsaur

(10) Patent No.: US 6,754,930 B1
(45) Date of Patent: Jun. 29, 2004

(54) MULTI-SECTIONAL APPLICATOR

(76) Inventor: Garry Tsaur, 19222 Tranbarger St., Rowland Heights, CA (US) 91748

(*) Notice: Subject to any disclaimer, the term of this patent is extended or adjusted under 35 U.S.C. 154(b) by 9 days.

(21) Appl. No.: 10/664,133

(22) Filed: Sep. 17, 2003

(51) Int. Cl.$^7$ .............................. A47L 13/12; A46B 5/00
(52) U.S. Cl. ....................... 15/118; 15/143.1; 15/210.1
(58) Field of Search ................................. 15/118, 143.1, 15/210.1

(56) References Cited

U.S. PATENT DOCUMENTS

| | | | | |
|---|---|---|---|---|
| 2,246,778 A | * | 6/1941 | Cahoon | 426/81 |
| 2,386,085 A | * | 10/1945 | Babel | 15/167.1 |
| 5,414,890 A | * | 5/1995 | Morando | 15/167.1 |
| 5,526,548 A | * | 6/1996 | Ostrowski | 15/431 |
| 6,049,934 A | * | 4/2000 | Discko | 15/106 |

* cited by examiner

Primary Examiner—Randall Chin
(74) Attorney, Agent, or Firm—Joe Nieh

(57) ABSTRACT

A swab applicator that may be selectively broken into shorter sections is disclosed. The multi-sectional applicator comprises of an elongated handle with applicator tips affixed to one or both of its ends. Multiple score lines are formed along the length of the elongated handle wherein the multi-sectional applicator may be selectively broken into shorter sections at the score lines. The end section with the applicator tip may be broken-off and disposed of after the applicator tip is used while retaining the remainder of the swab applicator and the other unused applicator tip for other applications or for sebsequent.

8 Claims, 1 Drawing Sheet

MULTI-SECTIONAL APPLICATOR

BACKGROUND

1. Field of Invention

The present invention relates generally to a swab applicator. More specifically the present invention relates to a swab applicator that may be selectively broken into shorter sections.

2. Description of Related Art

Swab applicator generally comprises of a tubular handle with a formed absorbent tip at one or both ends of the tubular handle. The absorbent tip may be made of cotton or a foam absorbent material. The tip may also be a brush. The tubular handle may be made of wood, paper, or plastic and it may be solid or hollow.

Swab applicators have a variety of applications. Swab applicators are a convenient and sanitary means for applying and removing a variety of substances such as liquids, lotions, creams, and various chemicals and medications. Generally the applicator tip of a dry swab applicator is first placed in contact with the liquid to be applied for the applicator tip to absorb the liquid. Subsequently, the moisturized applicator tip is placed in contact with the surface to apply the absorbed liquid to the surface. Swab applicators may also be used to remove substances such as makeup and other specimens by wiping the substance with the applicator tip to remove and retrieve the substance.

SUMMARY OF THE INVENTION

The present invention is a swab applicator that may be selectively broken into shorter sections. The multi-sectional applicator comprises of an elongated handle with applicator tips affixed to one or both of its ends and multiple score lines formed along the length of the elongated handle wherein the multi-sectional applicator may be selectively broken into shorter sections at the score lines. After an applicator tip is used, the end section with the used applicator tip may be broken-off and disposed of while retaining the remainder of the swab applicator and the other unused applicator tip for other applications or for subsequent uses.

DETAILED DESCRIPTION OF THE PREFERRED EMBODIMENT

Figure 1:
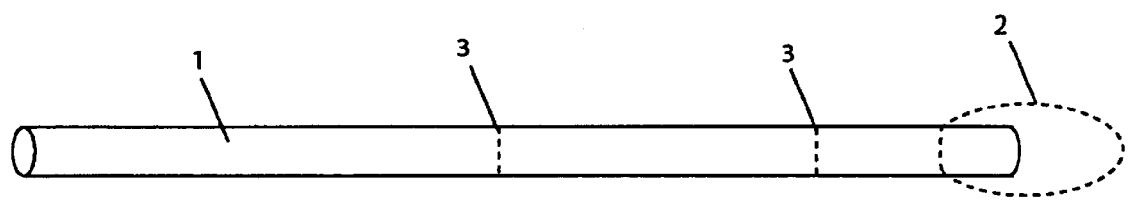
FIG. 1 shows the preferred embodiment of the multi-sectional applicator.
Figure 2:
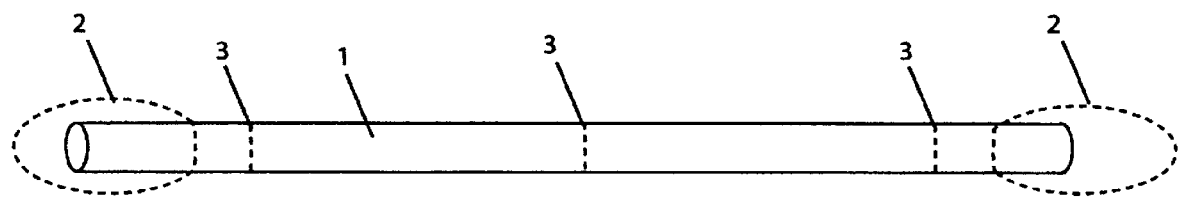
FIG. 2 shows another embodiment of the multi-sectional applicator.

FIG. 1 shows the preferred embodiment of the present invention. In the preferred embodiment, the multi-sectional applicator comprises of an elongated handle 1 with applicator tips 2 affixed to one or both of its ends, as shown in FIG. 2, and multiple score lines 3 formed along the length of the elongated handle 1 wherein the multi-sectional applicator may be selectively broken into shorter sections at the score lines 3. After an applicator tip 2 is used, the end section with the used applicator tip 2 may be broken-off and disposed of while retaining the remainder of the swab applicator and the other unused applicator tip for other applications or for subsequent uses. Furthermore, if the elongated handle 1 is hollow, after the applicator tips 2 are removed, the hollow elongated handle may be used as a straw or as a implement to retrieve a small quantity of liquid by inserting it into the liquid to be retrieved and then sealing the top end with a finger to retain the liquid in the hollow interior of the elongated handle.

Although the description above contains many specificities, these should not be construed as limiting the scope of the invention but as merely providing illustrations of some of the presently preferred embodiments of this invention. Thus the scope of the invention should be determined by the appended claims and their legal equivalents, rather than by the examples given.

What is claimed is:

1. A multi-sectional applicator comprising an elongated handle with an applicator tip affixed to one of its ends and multiple score lines formed along the length of the elongated handle wherein the multi-sectional applicator may be selectively broken into shorter sections at the score lines.

2. A multi-sectional applicator as in claim 1, wherein the applicator tip is made of an absorbent material.

3. A multi-sectional applicator as in claim 1, wherein-said elongated handle is hollow.

4. A multi-sectional applicator as in claim 3, wherein the applicator tip is made of an absorbent material.

5. A multi-sectional applicator comprising an elongated handle with an applicator tip affixed to each of the two ends of the elongated handle and multiple score lines formed along the length of the elongated handle wherein the multi-sectional applicator may be selectively broken into shorter sections at the score lines.

6. A multi-sectional applicator as in claim 5, wherein the applicator tip is made of an absorbent material.

7. A multi-sectional applicator as in claim 5, wherein said elongated handle is hollow.

8. A multi-sectional applicator as in claim 7, wherein the applicator tip is made of an absorbent material.

* * * * *